United States Patent
Xie

(10) Patent No.: US 10,273,161 B2
(45) Date of Patent: Apr. 30, 2019

(54) SYNTHESIS OF MFI FRAMEWORK TYPE MOLECULAR SIEVES

(71) Applicant: Chevron U.S.A. Inc., San Ramon, CA (US)

(72) Inventor: Dan Xie, Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 15/846,616

(22) Filed: Dec. 19, 2017

(65) Prior Publication Data

US 2018/0194637 A1 Jul. 12, 2018

Related U.S. Application Data

(60) Provisional application No. 62/445,070, filed on Jan. 11, 2017.

(51) Int. Cl.
| | |
|---|---|
| *C01B 39/40* | (2006.01) |
| *B01J 29/40* | (2006.01) |
| *C01B 39/02* | (2006.01) |
| *C07C 1/20* | (2006.01) |

(52) U.S. Cl.
CPC ............ *C01B 39/40* (2013.01); *C01B 39/026* (2013.01); *B01J 29/40* (2013.01); *C01P 2004/32* (2013.01); *C01P 2004/45* (2013.01); *C01P 2004/62* (2013.01); *C01P 2004/64* (2013.01); *C07C 1/20* (2013.01); *C07C 2529/40* (2013.01)

(58) Field of Classification Search
CPC ....... C01B 39/40; B01J 29/40; C01P 2004/62; C01P 2004/64
See application file for complete search history.

(56) References Cited

U.S. PATENT DOCUMENTS

| | | | |
|---|---|---|---|
| 3,702,886 A | 11/1972 | Argauer et al. | |
| RE29,948 E | 3/1979 | Dwyer et al. | |
| 4,585,638 A | 4/1986 | Kuhl | |
| 8,840,864 B2* | 9/2014 | Choi ................. | B01J 20/18 |
| | | | 423/709 |
| 2011/0117007 A1 | 5/2011 | Burton, Jr. | |
| 2015/0298981 A1 | 10/2015 | Burton et al. | |
| 2015/0298982 A1 | 10/2015 | Mertens et al. | |
| 2015/0328627 A1 | 11/2015 | Burton | |
| 2018/0078928 A1* | 3/2018 | Burton ................ | C01B 37/02 |
| 2018/0194638 A1* | 7/2018 | Xie .................... | C01B 37/02 |
| 2018/0251691 A1* | 9/2018 | Timken .............. | C10G 50/00 |
| 2018/0266233 A1* | 9/2018 | Ahmed .............. | E21B 47/042 |
| 2018/0272252 A1* | 9/2018 | Kelkar .............. | B01D 19/0042 |
| 2018/0272309 A1* | 9/2018 | Bhandarkar ........ | B01J 19/0013 |
| 2018/0275036 A1* | 9/2018 | Dwarakanath ....... | G01N 11/00 |

OTHER PUBLICATIONS

PCT International Search Report, International Patent Appl. No. PCT/US2017/067270, dated Mar. 1, 2018.
R. Singh and P.K Dutta "MFI: a Case Study of Zeolite Synthesis" In: "Handbook of Zeolite Science and Technology" (Editors: S.M. Auerbach, K.A. Carrado and P.K. Dutta), Marcel Dekker, Inc. 21-63 (2003).

\* cited by examiner

*Primary Examiner* — David M Brunsman
(74) *Attorney, Agent, or Firm* — Terrence M. Flaherty

(57) ABSTRACT

A method is provided for the synthesis of MFI framework type molecular sieves using 1,6-bis(cyclopropylmethyl)-1,1,6,6-tetramethylhexane-1,6-diaminium cations as a structure directing agent.

9 Claims, 2 Drawing Sheets

SYNTHESIS OF MFI FRAMEWORK TYPE MOLECULAR SIEVES

CROSS-REFERENCE TO RELATED APPLICATIONS

This application claims priority to U.S. Provisional Application Ser. No. 62/445,070 filed Jan. 11, 2017, which is herein incorporated by reference in its entirety.

TECHNICAL FIELD

The present disclosure is directed to the synthesis of a molecular sieve of MFI framework type and to the use of the resultant molecular sieve as an adsorbent and a catalyst for organic conversion reactions.

BACKGROUND

Molecular sieves are a commercially important class of crystalline materials having distinct crystal structures with ordered pore structures and characteristic X-ray diffraction patterns. Natural and synthetic crystalline molecular sieves are useful as catalysts and adsorbents. The adsorptive and catalytic properties of each molecular sieve are determined in part by the dimensions of its pores and cavities. Thus, the utility of a particular molecular sieve in a particular application depends at least partly on its crystal structure. Molecular sieves are especially useful in such applications as gas separation and organic conversion processes.

Molecular sieves identified by the International Zeolite Associate (IZA) as having the framework type MFI are known. ZSM-5 is a known crystalline MFI material and is useful as a catalyst in a variety of organic conversion reactions.

Crystalline ZSM-5 and its conventional preparation using tetrapropylammonium cations as a structure directing agent are taught by U.S. Pat. No. 3,702,886 and U.S. Pat. No. Re. 29,948.

In addition to tetrapropylammonium cations, a large number of other organic nitrogen-containing compounds, including certain diquaternary ammonium compounds, have been known to direct the synthesis of ZSM-5. For example, U.S. Pat. No. 4,585,638 discloses that the synthesis of ZSM-5 can be directed by the diquaternary cation $(alkyl)_3N^+(CH_2)_6N^+(alkyl)_3$, where the alkyl group is propyl or butyl.

For some acid-catalyzed reactions over molecular sieves, it is beneficial to reduce diffusion lengths of the reagent and/or product molecules by employing a molecular sieve with a reduced crystal size. Small crystals also have the benefit of providing high surface area.

Accordingly, there is a continued need for new methods for making molecular sieves of the MFI framework type, particularly small crystal forms of this material.

SUMMARY

In one aspect, there is provided a method of making a molecular sieve of MFI framework type, the method comprising: (a) providing a reaction mixture comprising: (1) a source of an oxide of a tetravalent element (T); (2) a source of an oxide of a trivalent element (X); (3) a source of a Group 1 or Group 2 metal (M); (4) a structure directing agent (Q) comprising 1,6-bis(cyclopropylmethyl)-1,1,6,6-tetramethylhexane-1,6-diaminium cations; (5) a source of hydroxide ions; and (6) water; and (b) subjecting the reaction mixture to crystallization conditions sufficient to form crystals of the molecular sieve.

In another aspect, there is provided a molecular sieve of MFI framework type and, in its as-synthesized form, comprising 1,6-bis(cyclopropylmethyl)-1,1,6,6-tetramethylhexane-1,6-diaminium cations in its pores.

In yet another aspect, there is provided a molecular sieve of MFI framework type characterized as spheroidal polycrystalline aggregates with a diameter of 100 to 300 nm, each aggregate comprising a plurality of crystallites having a crystallite size of 5 to 20 nm.

In a further aspect, there is provided a process for converting a feedstock comprising an organic compound to a conversion product, the process comprising contacting the feedstock with a catalyst at organic compound conversion conditions, the catalyst comprising an active form of the molecular sieve described herein.

DETAILED DESCRIPTION

Introduction

Figures 1A, 1B, 1C:
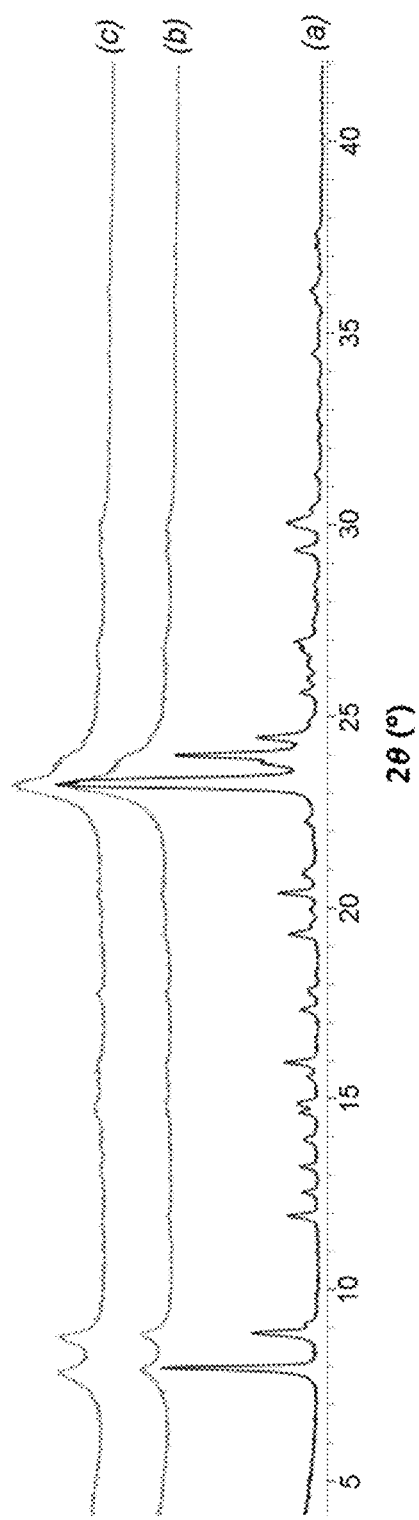
FIG. 1(a) is a powder X-ray diffraction (XRD) pattern of a conventional MFI framework type molecular sieve.
FIG. 1(b) is a powder XRD pattern of the as-synthesized molecular sieve product of Example 1.
FIG. 1(c) is powder XRD pattern of the calcined molecular sieve product of Example 1.

The term "framework type" is used in the sense described in the "*Atlas of Zeolite Framework Types*," Sixth Revised Edition, Elsevier, 2007.

The term "as-synthesized" is employed herein to refer to a molecular sieve in its form after crystallization, prior to removal of the structure directing agent.

The term "anhydrous" is employed herein to refer to a molecular sieve substantially devoid of both physically adsorbed and chemically adsorbed water.

The term "crystallite size" refers to the longest dimension of a crystal.

As used herein, the numbering scheme for the Periodic Table Groups is as disclosed in *Chem. Eng. News* 1985, 63(5), 26-27.

Reaction Mixture

In general, the present molecular sieve is synthesized by: (a) providing a reaction mixture comprising (1) a source of an oxide of a tetravalent element (T); (2) a source of an oxide of a trivalent element (X); (3) a source of a Group 1 or Group 2 metal (M); (4) a structure directing agent (Q) comprising 1,6-bis(cyclopropylmethyl)-1,1,6,6-tetramethylhexane-1,6-diaminium cations; (5) a source of hydroxide ions; and (6) water; and (b) subjecting the reaction mixture to crystallization conditions sufficient to form crystals of the molecular sieve.

The composition of the reaction mixture from which the molecular sieve is formed, in terms of molar ratios, is identified in Table 1 below:

TABLE 1

| Reactants | Useful | Exemplary |
|---|---|---|
| $TO_2/X_2O_3$ | ≥15 | 20 to 500 |
| $M/TO_2$ | 0.05 to 0.50 | 0.20 to 0.45 |

TABLE 1-continued

| Reactants | Useful | Exemplary |
|---|---|---|
| Q/TO$_2$ | 0.05 to 0.50 | 0.10 to 0.30 |
| OH/TO$_2$ | 0.05 to 0.50 | 0.20 to 0.45 |
| H$_2$O/TO$_2$ | 10 to 60 | 15 to 50 | wherein T, X, M and Q are as described herein above.

Suitable sources of the tetravalent element (T) depend on the element T selected. The tetravalent element (T) may be selected from silicon, germanium, and combinations thereof. Suitable sources of silicon include fumed silica, colloidal silica, precipitated silica, alkali metal silicates, and tetraalkyl orthosilicates. Suitable sources of germanium include germanium oxide and germanium ethoxide.

Suitable sources of the trivalent element (X) depend on the element X selected. The trivalent element (X) may be selected from one or more of boron, aluminum and gallium. Suitable sources of aluminum include hydrated alumina and water-soluble aluminum salts (e.g., aluminum nitrate).

Combined sources of T and X can additionally or alternatively be used and can include aluminosilicate zeolites (e.g., zeolite Y) and clays or treated clays (e.g., metakaolin).

The structure directing agent (Q) comprises 1,6-bis(cyclopropylmethyl)-1,1,6,6-tetramethylhexane-1,6-diaminium cations, represented by the following structure (1):

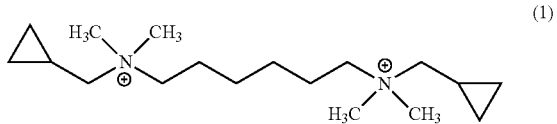 [SMILES: C[N+](C)(CCCCCC[N+](C)(C)CC1CC1)CC1CC1]

(1)

Suitable sources of Q include the hydroxides, chlorides, bromides, and/or other salts of the diquaternary ammonium compound.

Examples of suitable Group 1 or Group 2 metals (M) include sodium, potassium and calcium, with sodium being preferred. The metal (M) is generally present in the reaction mixture as the hydroxide.

The reaction mixture may also contain seeds of a molecular sieve material, such as ZSM-5, desirably in an amount of from 0.01 to 10,000 ppm by weight (e.g., from 100 to 5000 ppm by weight) of the reaction mixture.

For each embodiment described herein, the reaction mixture can be supplied by more than one source. Also, two or more reaction components can be provided by one source.

The reaction mixture can be prepared either batch wise or continuously. Crystal size, morphology and crystallization time of the crystalline molecular sieve can vary with the nature of the reaction mixture and the crystallization conditions.

Crystallization and Post-Synthesis Treatment

Crystallization of the molecular sieve from the above reaction mixture can be carried out under either static, tumbled or stirred conditions in a suitable reactor vessel, such as for example polypropylene jars or Teflon-lined or stainless steel autoclaves, at a temperature of from 125° C. to 200° C. for a time sufficient for crystallization to occur at the temperature used, e.g., from 3 to 10 days. Crystallization is usually carried out in closed system under autogenous pressure.

Once the molecular sieve crystals have formed, the solid product is recovered from the reaction mixture by standard mechanical separation techniques such as centrifugation or filtration. The crystals are water-washed and then dried to obtain the as-synthesized molecular sieve crystals. The drying step is typically performed at a temperature of less than 200° C.

As a result of the crystallization process, the recovered crystalline molecular sieve product contains within its pore structure at least a portion of the structure directing agent used in the synthesis.

The as-synthesized molecular sieve may be subjected to treatment to remove part or all of the structure directing agent used in its synthesis. This is conveniently effected by thermal treatment (calcination) in which the as-synthesized material is heated at a temperature of at least about 370° C. for at least 1 minute and generally not longer than 20 hours. The thermal treatment can be performed at a temperature up to about 925° C. While sub-atmospheric pressure can be employed for the thermal treatment, atmospheric pressure is desired for reasons of convenience. Additionally or alternatively, the structure directing agent can be removed by treatment with ozone (see, e.g., A. N. Parikh et al., *Micropor. Mesopor. Mater.* 2004, 76, 17-22). The organic-depleted product, especially in its metal, hydrogen and ammonium forms, is particularly useful in catalytic applications. The organic-depleted molecular sieve in its hydrogen form is referred to herein as the "active form" of the molecular sieve, with or without metal function present.

To the extent desired and depending upon the TO$_2$/X$_2$O$_3$ molar ratio, any Group 1 or Group 2 metal cations in the as-synthesized molecular sieve can be replaced in accordance with techniques well known in the art by ion exchange with other cations. Preferred replacing cations include metal ions, hydrogen ions, hydrogen precursor ions (e.g., ammonium ions), and combinations thereof. Particularly preferred replacing cations are those which tailor the catalytic activity for certain organic conversion reactions. These include hydrogen, rare earth metals and metals of Groups 2 to 15 of the Periodic Table of the Elements.

Characterization of the Molecular Sieve

In its as-synthesized and anhydrous form, the present molecular sieve has a chemical composition comprising the following molar relationship shown in Table 2:

TABLE 2

| | Broad | Exemplary |
|---|---|---|
| TO$_2$/X$_2$O$_3$ | ≥15 | 20 to 500 |
| Q/TO$_2$ | >0 to 0.1 | >0 to 0.1 | wherein T, X and Q are as described herein above.

The molecular sieve synthesized according to the present method will typically crystallize as spheroidal polycrystalline aggregates having a diameter of 300 nm or less (e.g., 100 to 300 nm), as determined by SEM. Each crystalline aggregate of the molecular sieve contains a plurality of substantially uniform crystallites. The crystallites have an average crystallite size of 20 nm of less (e.g., 5 to 20 nm, 10 to 20 nm, 5 to 17.5 nm, 10 to 17.5 nm, 10 to 15 nm, 12 to 20 nm, or 12 to 17.5 nm). Average crystallite size can be determined from powder XRD using the Scherrer equation.

The MFI framework type molecular sieves synthesized according to the present method are characterized by their powder XRD pattern. Powder XRD patterns representative of MFI framework type molecular sieves can be referenced in "*Collection of Simulated XRD Powder Patterns for Zeolites*" (Fifth Revised Edition, Elsevier, 2007), published on behalf of the Structure Commission of the International Zeolite Association. Minor variations in the diffraction pattern can result from variations in the molar ratios of the framework species of the particular sample due to changes in lattice constants. In addition, sufficiently small crystals will affect the shape and intensity of peaks, leading to significant peak broadening. Minor variations in the diffraction pattern can result from variations in the organic compound used in the preparation. Calcination can also cause minor shifts in the X-ray diffraction pattern.

The powder X-ray diffraction patterns presented herein were collected by standard techniques. The radiation was CuKα radiation. The peak heights and the positions, as a function of 2θ where θ is the Bragg angle, were read from the relative intensities of the peaks, and d, the interplanar spacing corresponding to the recorded lines, can be calculated.

Adsorption and Catalysis

The present molecular sieve can be used as an adsorbent or, particularly in its aluminosilicate form, as a catalyst to catalyze a wide variety of organic compound (e.g., hydrocarbon) conversion processes including many of present commercial/industrial importance. Examples of chemical conversion processes which are effectively catalyzed by the present molecular sieve are those where high acid activity and large surface area are important.

As in the case of many catalysts, it may be desirable to incorporate the present molecular sieve with another material resistant to the temperatures and other conditions employed in organic conversion processes. Such materials include active and inactive materials, and synthetic or naturally occurring zeolites, as well as, inorganic materials such as clays, silica and/or metal oxides such as alumina. The latter may be either naturally occurring or in the form of gelatinous precipitates or gels including mixtures of silica and metal oxides. Use of a material in conjunction with the present molecular sieve (i.e., combined therewith or present during synthesis of the new crystal, which is active) tends to change the conversion and/or selectivity of the catalyst in certain organic conversion processes. Inactive materials suitably serve as diluents to control the amount of conversion in a given process so that products can be obtained in an economic and orderly manner without employing other means for controlling the rate of reaction. These materials may be incorporated into naturally occurring clays (e.g., bentonite and kaolin) to improve the crush strength of the catalyst under commercial operating conditions. These materials (i.e., clays, oxides, etc.) function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the present molecular sieve include the montmorillonite and kaolin family, which families include the sub-bentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined, or initially subjected to calcination, acid treatment or chemical modification. Binders useful for compositing with the present molecular sieve also include inorganic oxides, such as silica, zirconia, titania, magnesia, beryllia, alumina, and mixtures thereof.

In addition to the foregoing materials, the present molecular sieve can be composited with a porous matrix material such as silica-alumina, silica-magnesia, silica-zirconia, silica-thoria, silica-beryllia, silica-titania, as well as, ternary compositions such as silica-alumina-thoria, silica-alumina-zirconia, silica-alumina-magnesia and silica-magnesia-zirconia.

The relative proportions of the present MFI framework type molecular sieve and inorganic oxide matrix may vary widely, with the MFI framework type molecular sieve content ranging from 1 to 90% by weight (e.g., 2 to 80% by weight) of the composite.

EXAMPLES

The following illustrative examples are intended to be non-limiting.

Example 1

22.33 g of deionized water, 9.48 g of a 16.14% 1,6-bis (cyclopropylmethyl)-1,1,6,6-tetramethylhexane-1,6-diaminium hydroxide solution, 0.39 g of a 50% NaOH solution and 3.00 g of CBV760 Y-zeolite powder (Zeolyst International; $SiO_2/Al_2O_3$ molar ratio=60) were mixed together in a Teflon liner. The resulting gel was stirred until it became homogeneous. The liner was then capped and placed with a Parr steel autoclave reactor. The autoclave was then placed in an oven and heated at 160° C. for 6 days with tumbling at 43 rpm. The solid products were recovered from the cooled reactor by centrifugation, washed with deionized water and dried at 95° C.

The resulting zeolite product was analyzed by powder XRD and SEM. FIG. 1(*a*) is a powder of a conventional MFI framework type molecular sieve. FIG. 1(*b*) is powder XRD pattern of the as-synthesized molecular sieve and is consistent with the material being a pure MFI framework type molecular sieve having significantly decreased crystal size as inferred from the peak broadening in the powder XRD pattern.

The as-synthesized molecular sieve of Example 1 was calcined inside a muffle furnace under a flow of air heated to 595° C. at a rate of 1° C./minute and held at 595° C. for 5 hours, cooled and then analyzed by powder XRD. The powder XRD pattern of the calcined molecular sieve is shown in FIG. 1(*c*) and indicated that the material remains stable after calcination to remove the structure directing agent.

Figure 2:
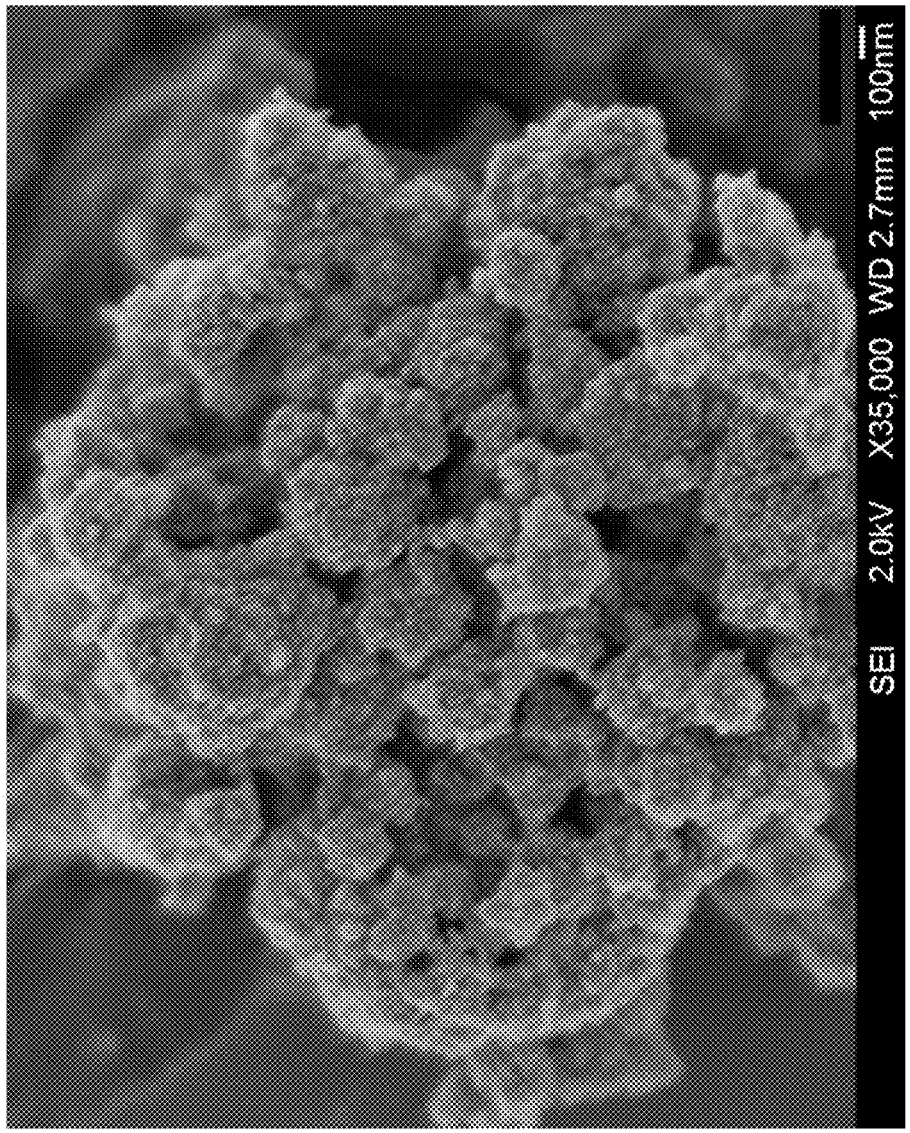
FIG. 2 is a Scanning Electron Micrograph (SEM) image of the as-synthesized molecular sieve product of Example 1.

FIG. 2 is a SEM image of the as-synthesized molecular sieve and indicates a uniform field of crystals. The SEM image appeared to show that the product was composed of spheroidal polycrystalline aggregates having a size of about ≤300 nm. The individual crystallites within each aggregate appeared to have a crystallite size of ≤20 nm. The average crystallite size was determined to be 13.4 nm from the powder XRD pattern shown in FIG. 1(*b*) using the Scherrer equation.

The product had a $SiO_2/Al_2O_3$ molar ratio of 39.8, as determined by ICP elemental analysis.

Example 2

36.70 g of deionized water, 15.80 g of a 16.14% 1,6-bis (cyclopropylmethyl)-1,1,6,6-tetramethylhexane-1,6-diaminium hydroxide solution, 1.51 g of a 45% KOH solution and 5.00 g of CBV720 Y-zeolite powder (Zeolyst International; $SiO_2/Al_2O_3$ molar ratio=30) were mixed together in a Teflon liner. The resulting gel was stirred until it became homogeneous. The liner was then capped and placed with a Parr steel autoclave reactor. The autoclave was then placed in an oven and heated at 160° C. for 6 days with tumbling at 43 rpm. The solid products were recovered from the cooled reactor by centrifugation, washed with deionized water and dried at 95° C.

The resulting zeolite product was identified by powder XRD as a pure MFI framework type molecular sieve.

SEM analysis (not shown) indicated a uniform field of crystals having a morphology and size consistent with the material described in Example 1.

The product had a $SiO_2/Al_2O_3$ molar ratio of 23, as determined by ICP elemental analysis.

Example 3

16.17 g of deionized water, 9.80 g of a 16.14% 1,6-bis(cyclopropylmethyl)-1,1,6,6-tetramethylhexane-1,6-diaminium hydroxide solution, 0.40 g of a 50% NaOH solution, 10.00 g of LUDOX® AS-30 colloidal silica and 0.20 g of Reheis F-2000 hydrated alumina were mixed together in a Teflon liner. The resulting gel was stirred until it became homogeneous. The liner was then capped and placed with a Parr steel autoclave reactor. The autoclave was then placed in an oven and heated at 170° C. for 7 days with tumbling at 43 rpm. The solid products were recovered from the cooled reactor by centrifugation, washed with deionized water and dried at 95° C.

The resulting zeolite product was identified by powder XRD as a pure MFI framework type molecular sieve.

SEM analysis (not shown) indicated a uniform field of crystals having a morphology and size consistent with the material described in Example 1.

The product had a $SiO_2/Al_2O_3$ molar ratio of 43.7, as determined by ICP elemental analysis.

Example 4

16.23 g of deionized water, 9.80 g of a 16.14% 1,6-bis(cyclopropylmethyl)-1,1,6,6-tetramethylhexane-1,6-diaminium hydroxide solution, 0.40 g of a 50% NaOH solution, 10.00 g of LUDOX® AS-30 colloidal silica and 0.07 g of Reheis F-2000 hydrated alumina were mixed together in a Teflon liner. The resulting gel was stirred until it became homogeneous. The liner was then capped and placed with a Parr steel autoclave reactor. The autoclave was then placed in an oven and heated at 170° C. for 7 days with tumbling at 43 rpm. The solid products were recovered from the cooled reactor by centrifugation, washed with deionized water and dried at 95° C.

The resulting zeolite product was identified by powder XRD as a pure MFI framework type molecular sieve.

SEM analysis (not shown) indicated a uniform field of crystals having a morphology and size consistent with the material described in Example 1.

The product had a $SiO_2/Al_2O_3$ molar ratio of 126.2, as determined by ICP elemental analysis.

Example 5

A portion of the calcined MFI framework type molecular sieve of Example 1 was subjected to a micropore volume analysis using $N_2$ as adsorbate and via the B.E.T. method. The molecular sieve exhibited a micropore volume of 0.11 $cm^3/g$.

The invention claimed is:

1. A method of making a molecular sieve of MFI framework type, the method comprising:
    (a) providing a reaction mixture comprising:
        (1) a source of an oxide of a tetravalent element (T);
        (2) a source of an oxide of a trivalent element (X);
        (3) a source of a Group 1 or Group 2 metal (M);
        (4) a structure directing agent (Q) comprising 1,6-bis(cyclopropylmethyl)-1,1,6,6-tetramethylhexane-1,6-diaminium cations;
        (5) a source of hydroxide ions; and
        (6) water; and
    (b) subjecting the reaction mixture to crystallization conditions sufficient to form crystals of the molecular sieve.

2. The method of claim 1, wherein the reaction mixture has a composition, in terms of molar ratios, as follows:

| | |
|---|---|
| $TO_2/X_2O_3$ | ≥15 |
| $M/TO_2$ | 0.05 to 0.50 |
| $Q/TO_2$ | 0.05 to 0.50 |
| $OH/TO_2$ | 0.05 to 0.50 |
| $H_2O/SiO_2$ | 10 to 60. |

3. The method of claim 1, wherein the reaction mixture has a composition, in terms of molar ratios, as follows:

| | |
|---|---|
| $TO_2/X_2O_3$ | 20 to 500 |
| $M/TO_2$ | 0.20 to 0.45 |
| $Q/TO_2$ | 0.10 to 0.30 |
| $OH/TO_2$ | 0.20 to 0.45 |
| $H_2O/TO_2$ | 15 to 50. |

4. The method of claim 1, wherein the tetravalent element (T) comprises silicon and the trivalent element (X) comprises aluminum.

5. The method of claim 1, wherein the crystallization conditions include a temperature of from 125° C. to 200° C.

6. A molecular sieve of MFI framework type and, in its as-synthesized form, comprising 1,6-bis(cyclopropylmethyl)-1,1,6,6-tetramethylhexane-1,6-diaminium cations in its pores.

7. The molecular sieve of claim 6, and having a $SiO_2/Al_2O_3$ molar ratio of at least 15.

8. The molecular sieve of claim 6, and having a $SiO_2/Al_2O_3$ molar ratio of 20 to 500.

9. The molecular sieve of claim 6, characterized as spheroidal polycrystalline aggregates having a diameter of 100 to 300 nm, each aggregate comprising a plurality of crystallites having an average crystallite size of 5 to 20 nm.

* * * * *